United States Patent [19]

Kula et al.

[11] Patent Number: 4,607,636
[45] Date of Patent: Aug. 26, 1986

[54] SURGICAL INSTRUMENT FOR APPLYING FASTENERS HAVING TISSUE LOCKING MEANS FOR MAINTAINING THE TISSUE IN THE INSTRUMENT WHILE APPLYING THE FASTENERS (CASE I)

[75] Inventors: John Kula, Budd Lake; Anthony S. Miksza, Jr., Jersey City, both of N.J.

[73] Assignee: Ethicon, Inc., Somerville, N.J.

[21] Appl. No.: 631,121

[22] Filed: Jul. 16, 1984

[51] Int. Cl.⁴ .................. A61B 17/00; A61B 17/12
[52] U.S. Cl. ........................ 128/334 R; 128/334 C; 227/DIG. 1
[58] Field of Search .............. 128/334 R, 334 C; 227/DIG. 1

[56] References Cited

U.S. PATENT DOCUMENTS

4,448,194  5/1984  DiGiovanni ............... 128/334 R
4,470,532  9/1984  Froehlich ................. 128/334 R X
4,508,253  4/1985  Green ........................ 227/19

Primary Examiner—Lucille M. Phynes
Attorney, Agent, or Firm—Robert L. Minier

[57] ABSTRACT

A surgical instrument for applying tissue fasteners. The instrument includes a stationary jaw and a movable jaw mounted on a support body. The jaws are placed on the opposite sides of the tissue to be joined. The instrument includes means for holding the tissue between the jaws while the fasteners are being applied and to provide rigidity between the jaws.

6 Claims, 18 Drawing Figures

SURGICAL INSTRUMENT FOR APPLYING FASTENERS HAVING TISSUE LOCKING MEANS FOR MAINTAINING THE TISSUE IN THE INSTRUMENT WHILE APPLYING THE FASTENERS (CASE I)

This invention relates to medical instruments and more particularly to instruments for joining tissue organs using fasteners. Preferably, the fasteners are two-piece with one part of the fastener a U-shaped staple and the other part of the fastener a receiver which interlocks with the legs of the staple to form the fastener.

BACKGROUND OF THE INVENTION

Over the years various surgical instruments for joining tissue have been developed. Most instruments have been developed utilizing metal staples for joining the tissue. The metal staples are relatively rigid, have their legs sharpened to readily penetrate the tissue, and once penetrated may then be crimped into a clinched position to hold the tissue together as is well known in the art. Instruments of this type are more fully disclosed and described in U.S. Pat. Nos. 3,080,564, 3,079,606, 2,891,250, 3,589,589, 4,207,898 and 4,351,466.

Generally, the instruments comprise a movable member or jaw and a stationary member or jaw. The movable jaw usually carries the metal staples and the stationary jaw carries an anvil which clinches or bends the legs of the staple that pass through the tissue. In use, the tissue is placed between the jaws, the jaws brought to the appropriate gap and the staples driven through the tissue and clinched to set the staple. A major problem with these instruments is the use of the metal staple. While metal staples provide desired hemostatsis in the joining of the tissue, they remain in the tissue and can disrupt future diagnostic techniques such as X-ray diagnosis, computer axial tomography, nuclear magnetic resonance, and the like. To eliminate this problem, it has been found desirable to develop instruments which can set non-metallic fasteners. These are fasteners made from biologically absorbable or non-absorbable polymeric materials. Examples of such non-absorbable polymeric materials would be the polyolefins, polyesters, and the like. Examples of the absorbable polymeric materials would be the polymers and copolymers of glycolide, lactide, dioxanone, etc. These polymeric materials do not have the dead-bend morphology of a metal and, hence, they cannot be clinched in the same manner as a metal staple. To use these polymers, the fasteners are designed as two-piece fasteners. This means one piece of the fastener is placed on one side of the tissue to be joined and the second piece of the fastener is placed on the other side of the tissue to be joined. One piece of the fastener is a U-shaped staple which has legs which are caused to penetrate the tissue. On the opposite side of the tissue is the second fastener piece or receiver which is a member used to engage the legs to interlock therewith once the legs have penetrated the tissue and, hence, join the tissue together.

As can be appreciated this major change in design and configuration of fasteners causes a number of problems. First, the fasteners must be designed to be sufficiently sharp and strong to penetrate the tissue or in certain instances some aiding means must be used with the fastener to assist in penetrating the tissue. Also, the fasteners must be designed to develop an interlocking between the two pieces.

These differences cause various types of forces to be used when joining the tissue together, and these forces are different from the forces required when joining tissue using metallic fasteners. Also, when utlizing the two-piece fasteners, alignment between the two fasteners is extremely critical. As can be appreciated, when applying these fasteners the instrument must hold the pieces until one piece has penetrated the tissue and the opposite piece is interengaged and locked on to the penetrating portion of the other member. Once this is accomplished the instrument must then release both pieces preferably simultaneously. An object of the present invention is to provide an instrument that has a stationary jaw and a movable jaw which may be easily and readily aligned when placed on opposite sides of tissue to be joined. A further object of the present invention is to provide an instrument where it is required the jaws be properly aligned before the fasteners may be placed. It is a further object of the present invention to provide a suitable instrument which can accept and control the various forces required when placing two-piece non-metallic fasteners. It is also an object of the present invention to provide both staples and fasteners which can be readily aligned and interengaged when used in the instruments of the present invention. Further objects and purposes of the present invention will be readily apparent from the following detailed description.

SUMMARY OF THE PRESENT INVENTION

The present invention provides a surgical instrument for joining tissue by means of staples or other fasteners. The fasteners may comprise a U-shaped staple member with or without a receiver for engaging with the legs of said staple member. The instrument places the staple member on one side of the tissue to be joined and the receiver, if one is used, on the opposite side of the tissue. The instrument causes the staple legs to penetrate the tissue and engage and interlock with the receiver or it may merely crimp the staple legs when no receiver is used. The instrument comprises a support body. Mounted at one end of the support body is a pair of jaws. A staple housing is mounted in one of the jaws and this jaw is movable with respect to the other of said jaws. Means are mounted in the support body for moving the jaw housing the staples towards the stationary jaw to close the gap between the jaws and clasp the tissue therebetween. Drive means are mounted on the support body for driving the staples from the jaw in which the staple housing is mounted towards the opposite jaw. Actuating means are mounted at the end of the support body opposite the end at which the jaws are mounted for actuating the staple drive means. Cooperating with the open end of the jaws is a means to hold tissue in place between the jaws while the staples are being driven. This tissue holding means passes through the movable jaw and interlocks with the stationary jaw to provide rigidity therebetween and to prevent misalignment of the jaws either before or during the operation. In a preferred embodiment of the present invention, the staple drive means is only actuable when the tissue holding means has properly aligned the pair of jaws. In certain embodiments of the present invention the tissue holding means is automatically released after the staple drive means has been actuated. Other features and details of the present invention will be discussed in the ensuing detailed description and drawing.

DETAILED DESCRIPTION OF THE DRAWINGS

Figures 1, 2, 3:
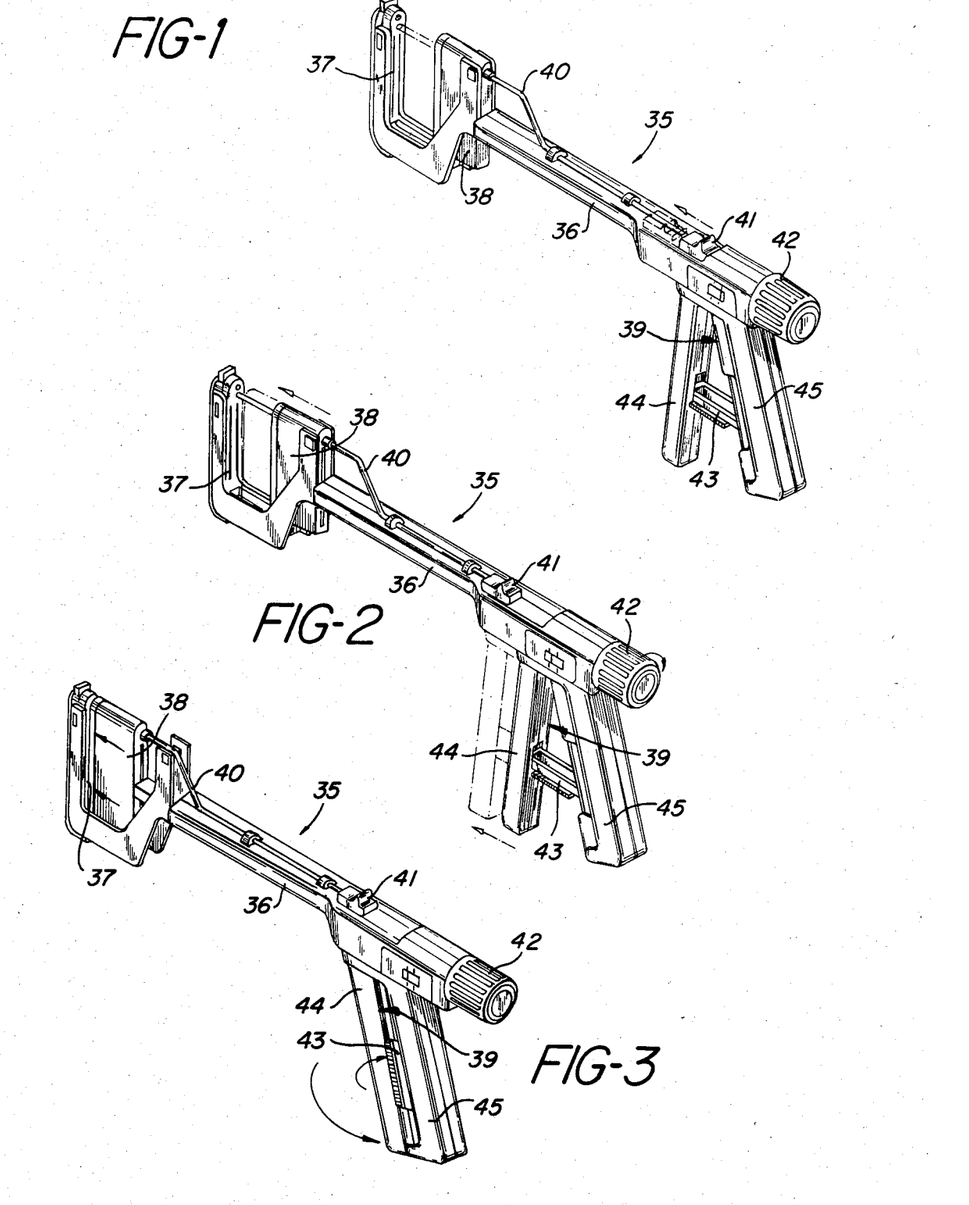
FIG. 1 is a perspective view of an instrument according to the present invention in its fully opened position.
FIG. 2 is a perspective view of the instrument of FIG. 1 in a partially open position.
FIG. 3 is a perspective view of the instrument of FIG. 1 in its firing position.

Referring to the drawings, in FIGS. 1, 2 and 3 there is depicted a surgical instrument 35 of the present invention useful for joining tissue. The instrument is depicted in three different positions.

In FIG. 1, the instrument is shown in the fully open position. The instrument comprises a support body, 36. A pair of jaws 37 and 38 are positioned at one end of the support body. Mounted the opposite end of the support body is means 39 for actuating the instrument. In FIG. 1, the jaws of the instrument are in the open position ready to be placed about the tissue to be joined.

In FIG. 2, the jaws have been moved closer to one another to produce an appropriate gap to clamp tissue in position between the jaws so that the tissue is ready to be stitched together.

FIG. 3 shows the instrument after it has been actuated and the tissue has been joined by the instrument.

One of the jaws 37 is stationarily mounted at one end of the support body 36. This jaw carries a plurality of receivers of the two-part fastening members used with the instruments of the present invention. The opposite jaw 38, carries the U-shaped fastening members, and is movably mounted on the support body. The tissue to be joined is placed between the two jaws and the movable jaw positioned with respect to the stationary jaw at an appropriate gap. Once the tissue is placed between the jaws, the locking arm 40 is moved forwardly by the pusher 41 to insure that the tissue is held between the jaws. Once the arm is set and engaged by the stationary jaw, the knob 42 at the opposite end of the support body is turned to move the movable jaw towards the stationary jaw and set the appropriate gap between the jaws. Once the gap has been appropriately set, the trigger locking lever 43 may be disengaged and the movable portion 44 of the actuating trigger means moved towards the stationary portion 45 of the trigger means to cause an appropriate pusher to drive the staples forward causing the legs of the staples to penetrate the tissue between the jaws and the legs of the staples to enter the appropriate receiver held in the stationary jaw. Once this is accomplished the knob 42 may be turned in the opposite direction to open the jaws, the locking lever 43 pushed back and the joined tissue separated from the jaws of the instrument.

Figure 4:
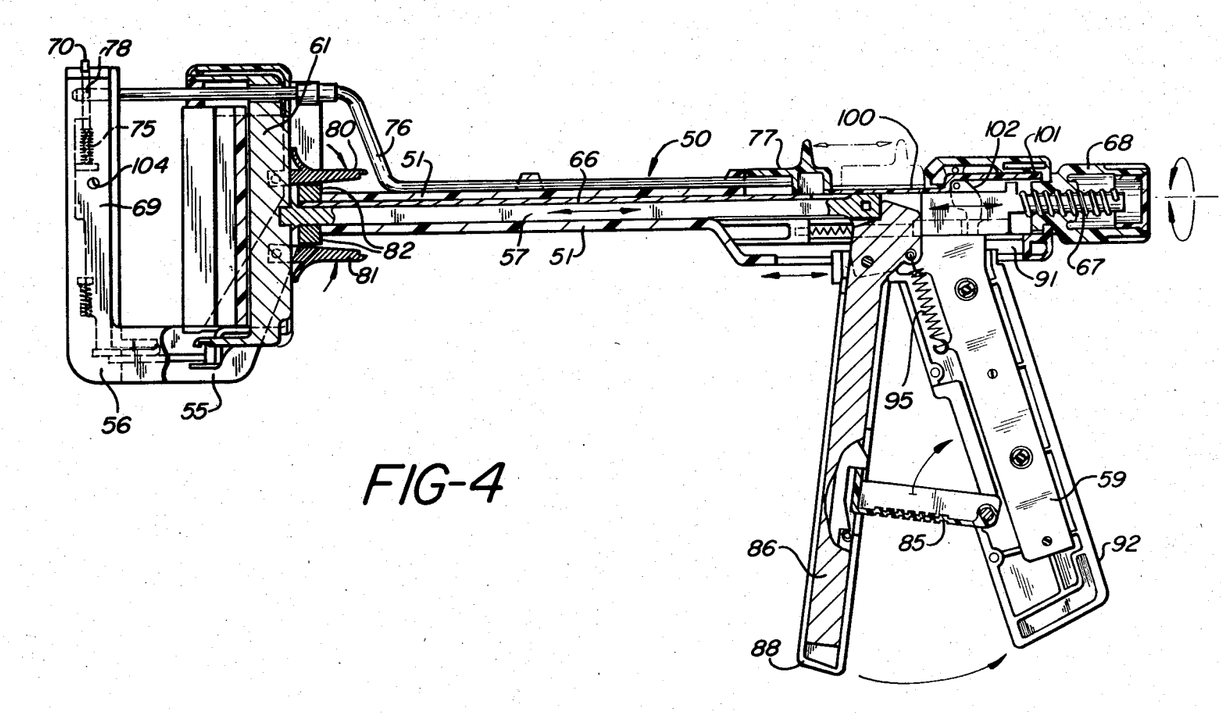
FIG. 4 is a cross-sectional view of another embodiment of a surgical instrument according to the present invention.
Figure 5:
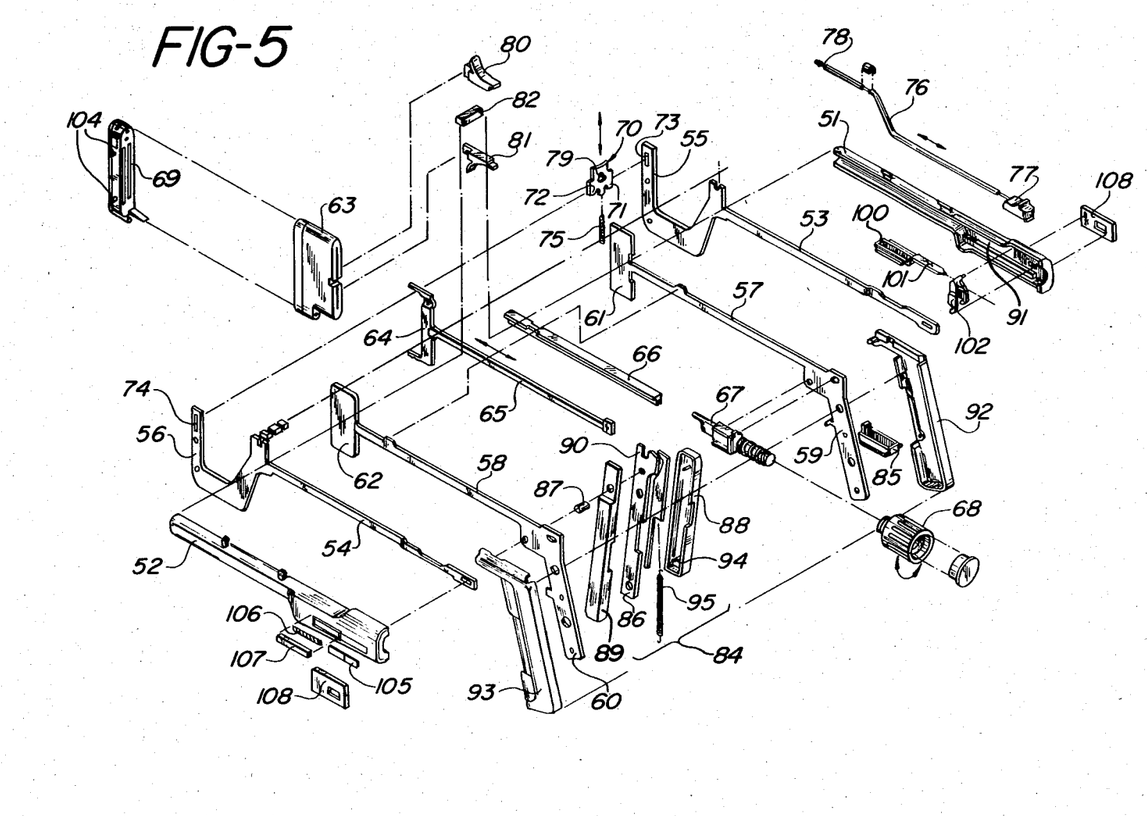
FIG. 5 is an exploded perspective view of the surgical instrument of FIG. 4.

FIG. 4 is a cross-sectional view of one embodiment of a surgical instrument according to the present invention and FIG. 5 is an exploded perspective view showing the different parts of the surgical instrument shown in FIG. 4. The body 50 of the instrument comprises a pair of outer cover members 51 and 52 which when pressed together form a hollow opening longitudinally disposed therebetween. Mounted in this opening are a pair of shafts 53 and 54 which, at one end, carry stationary supports 55 and 56 which together form the stationary jaw. The jaw is held together by riveted pins 104 located in holder 69. Also carried in the opening is a second pair of shafts 57 and 58 which carry at one end the supports 59 and 60 for the stationary portion of the actuating means and at the opposite end carry the supports 61 and 62 for the movable jaw. A holder 69 for the receiver portions of the fasteners is mounted between the stationary jaw supports and the holder 63 for the U-shaped staple portion of the fasteners is mounted between the movable jaw supports 61 and 62. A pusher 64 is mounted on a shaft 65 disposed in the center of the opening formed by the outer cover members. Mounted on top of the center shaft 65 is a movable member 66. The movable member is appropriately mounted through a screw 67 to the knob 68. Turning of the knob in one direction moves the pusher and the staple holder forwardly towards the receiver holder to set an appropriate gap between the staples and the receivers. Turning the knob in the opposite direction moves the pusher and staple holder away from the receiver holder to open the gap and allow tissue to be removed from between the staple holder and receiver holders.

Mounted between the supporting jaw members at the top thereof is a portion of means for holding tissue between the jaws and for locking the top of the jaws together to provide rigidity. This portion comprises a movable slotted member 70 having a pair of ears 71 and 72. The ears are disposed in slots 73 and 74 disposed in stationary supports 55 and 56. A compression spring 75 is mounted beneath the slotted member to allow the member to move up and down in the slots disposed in the stationary jaw members. Mounted on top of the outer cover members 51 and 52 and longitudinally thereto is the cooperating portion of the means for holding tissue and locking the jaws together for rigidity. This cooperating portion is a longitudinal movable member 76 that fits through an opening in the upper portion staple holder member 63. The longitudinally movable member is movable forwards and backwards with respect to the outer cover and is moved by the thumbs press 77. The movable member has a slot 78 at its free end and when moved forwardly, interlocks with the opening 58 in the movable slot member 70. A dog depends from the thumb press and fits into grooved member 100 mounted at the back and on top of the cover members. At the opposite end of the groove is a portion 101 that extends inwardly and engages in a slot in the knob 68. The portion 101 is guided in its movement by outer covers 51 and 52. Until the member is pushed as far forwardly as possible to remove the portion 101 from the slot in the knob, the knob cannot be rotated. Mounted from the staple holder are a pair of pawls 80 and 81 and mounted on the rigid shifts 53 and 54 is an anchor 82. The pawls are so disposed as to interlock with the anchor when the appropriate gap is set between the staple holding member 63 and the receiving holding member 69. The interlocking pawls and anchor provide added rigidity to the instrument and allow greater forces to be used when driving the staples through the tissue and into locking relationship with the receivers. At the opposite end of the instrument is mounted the trigger or actuating means 84. The actuating means comprises a movable trigger portion mounted between the supports 57 and 58 by a pin 87. A pivotal member 86 is encased by interlocking plastic handle halves 88 and 89 of the movable trigger. The pivotal member 86 includes an ear 90 which engages the shaft 65. The actuating means 84, members 61 and 62 and the shaft 65 are slideably mounted in slot 91 in the outer cover members 51 and 52. The stationary trigger portion comprises a pair of plastic handle halves 92 and 93. Mounted between the pivotal trigger and the stationary trigger is a pivotal interlocking member 85. This member is pivotally mounted between the stationary handles 92 and 93 and interlocks by engaging a pin 94 and spring 95 mounted in the movable portion of the trigger member. Mounted in the cover member 52 is a gauge to tell when the correct gap is attained between the receiver holder and the staple holder. The gauge comprises a marked member 105 that is linked to the screw member 67 and is mounted in position on the cover member 52 by a spring 106 and cover plate 107. Appropriate cover plate 108 is for identification and to see the mark on the marked member are placed on the outside of the cover members.

Figure 6:
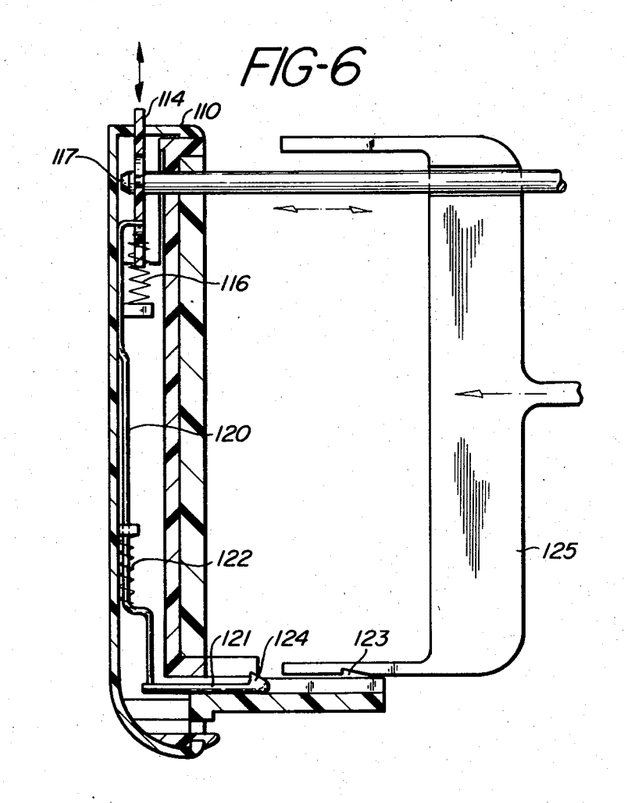
FIG. 6 is a cross-sectional view of one type of tissue and jaw locking and aligning mechanism with the jaws in the open position.
Figure 7:
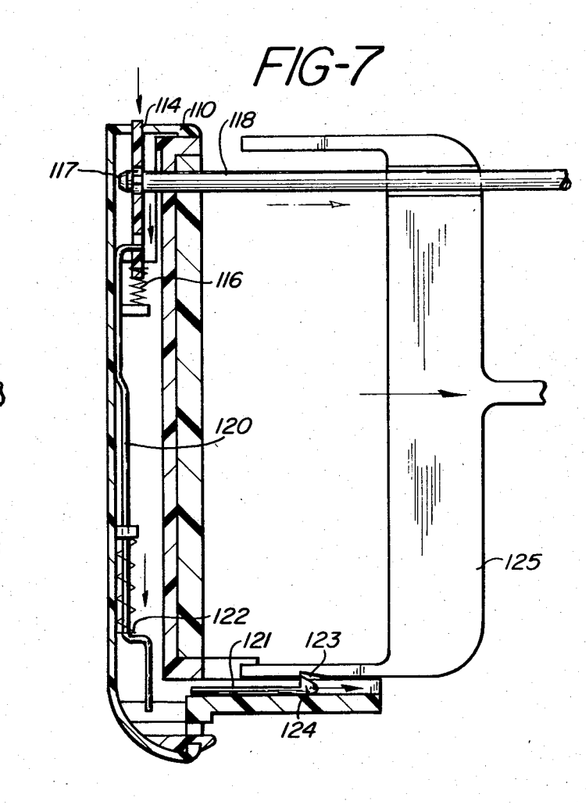
FIG. 7 is a cross-sectional view of the mechanism of FIG. 6 with the jaws in the closed position.
Figure 8:
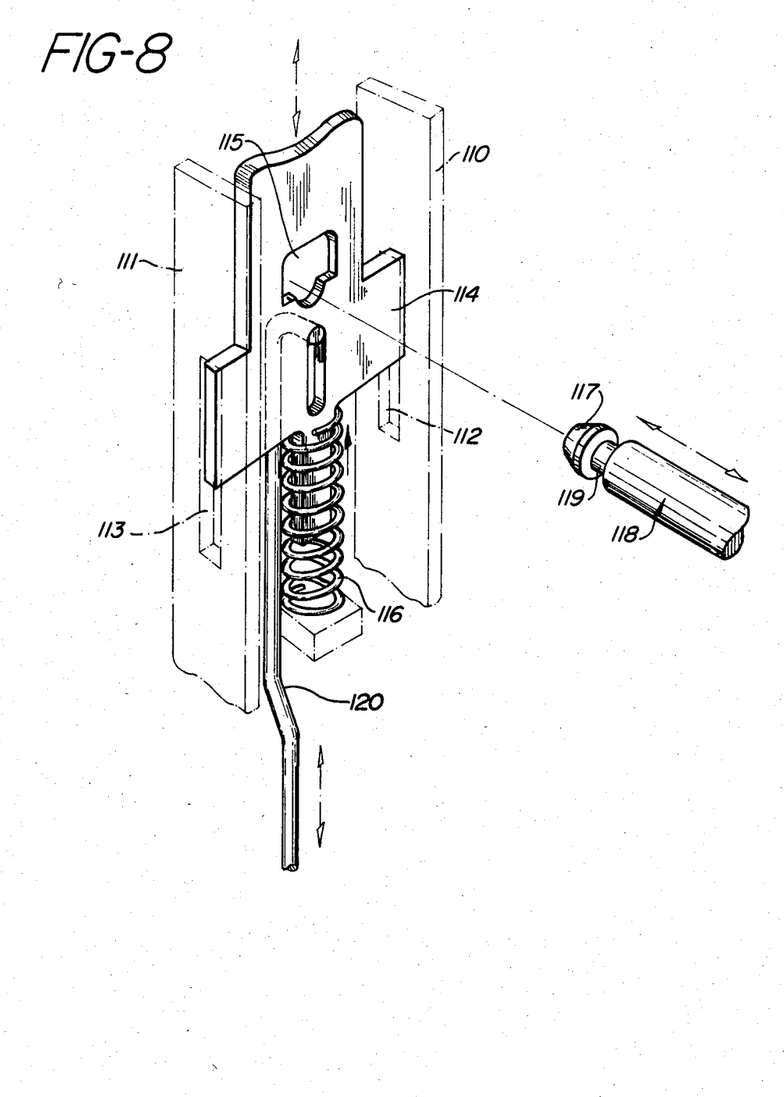
FIG. 8 is an exploded perspective view of a portion of the mechanism shown in FIGS. 6 and 7.

The means which holds the tissue between the oppositely opposed jaws provides improved rigidity to the pair of jaws and interlocks to prevent firing of the fasteners prior to the appropriate gap being set between the fasteners. The mechanism also aligns the jaws. An embodiment that automatically releases when the jaws are reopened is clearly depicted in the cross-sectional figures shown in FIGS. 6 and 7 and the perspective view shown in FIG. 8. As may be seen in these Figures, the stationary jaw comprises a pair of support members 110 and 111. Mounted between these support members, movably in a vertical position, between a slot 112 and 113 in each member is an interlocking member 114. That member 114 also has a slot 115 in it and is compressibly positioned at the upper portion of the slots 112 and 113 by compression spring 116. A downward force will allow the member 114 to move in the slots downwardly against the compression spring. This downward force is applied by the beveled edge 117 of the interlocking pin 118. The pin includes a groove 119 at its end to engage with the member 114. Until the groove in the interlocking pin meets the opening in the movable member and aligns the jaws, the gap between the jaws cannot be set. Linked to the interlocking member 114 is a spring operated releasing lever 120. Holding the releasing lever in its closed position is a movable member 121. The releasing lever is mounted via a spring 122 on the movable member. When the movable jaw 125 is moved to the appropriate gap with the stationary jaw an indent 123 on the jaw 125 engages an ear 124 on the movable member. When the jaws are separated after the fasteners have been placed in the tissue, the movable member is disengaged from the releasing lever and the member 114 drops in the slots and releases the pin 118 which can be pulled backwardly releasing the tissue from between the jaws.

Figure 9:
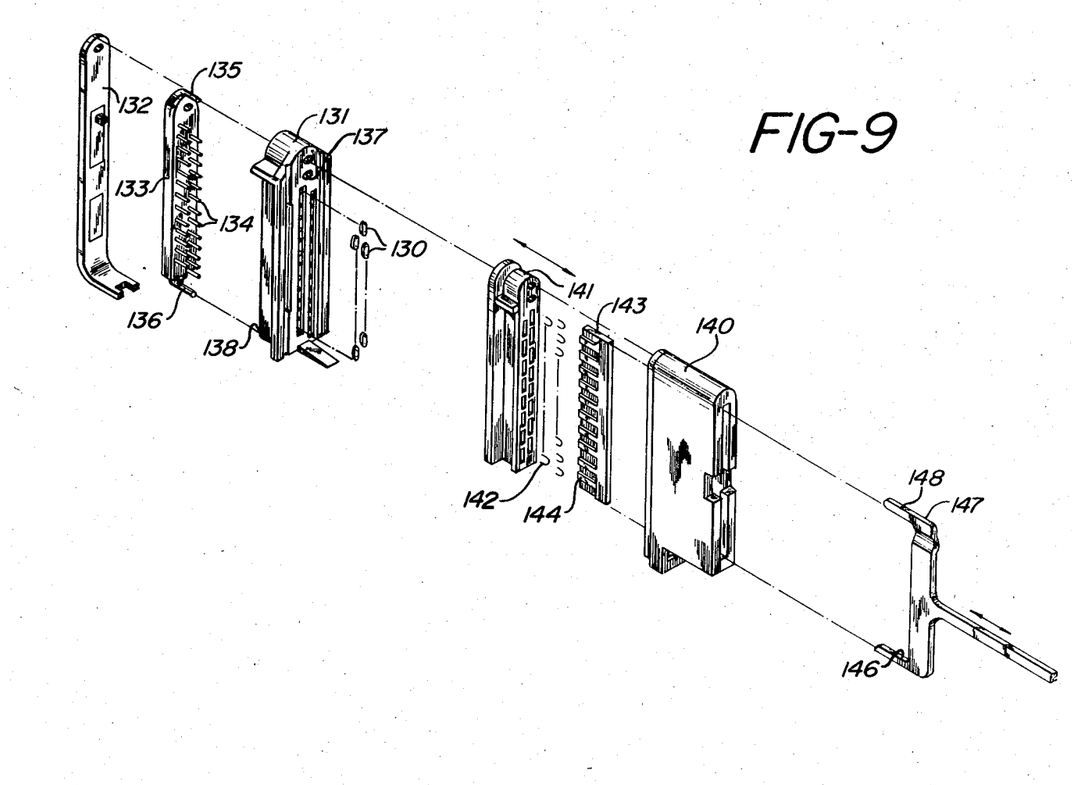
FIG. 9 is an exploded perspective view of the working parts of one embodiment of the jaws of an instrument of the present invention.

Referring to FIG. 9 there is shown an exploded perspective view of one embodiment of the working parts of the pair of jaws of instruments according to the present invention. Receivers, and in this instance they comprise members having a pair of openings disposed therein, are mounted in a stationary jaw and U-shaped staples with the legs of the U designed to enter the openings of the receivers are mounted in the movable jaw. The receivers 130 are mounted in a housing 131 mounted on the stationary jaw 132. The receivers are held in that housing by a movable member 133 which has pins 134 which frictionally engage the openings in the receivers. This holding member is movably mounted by virtue of an upper and a lower pin 135 and 136 respectively positioned in openings 137 and 138 in the receiver housing 131. The movable jaw 140 carries a housing 141 for holding the U-shaped staples 142. Mounted behind this housing is a first pusher means 143 having fingers 144 which engage the back end or the span of the U-shaped staples. Second drive means 147 mounted at the rear of the jaw moves forwardly to drive the first drive means and push the staples out of the housing so that the legs of the staples engage the receiver. Along therewith pins 142 and 148 of the second drive means engage the pins 135 and 136 and push the pins through the opening in the housing into the receiving housing opening to push the pins 135 and 136 out of frictional engagement with the receivers thus allowing the receivers to interlock with the legs of the staple.

Figure 10:
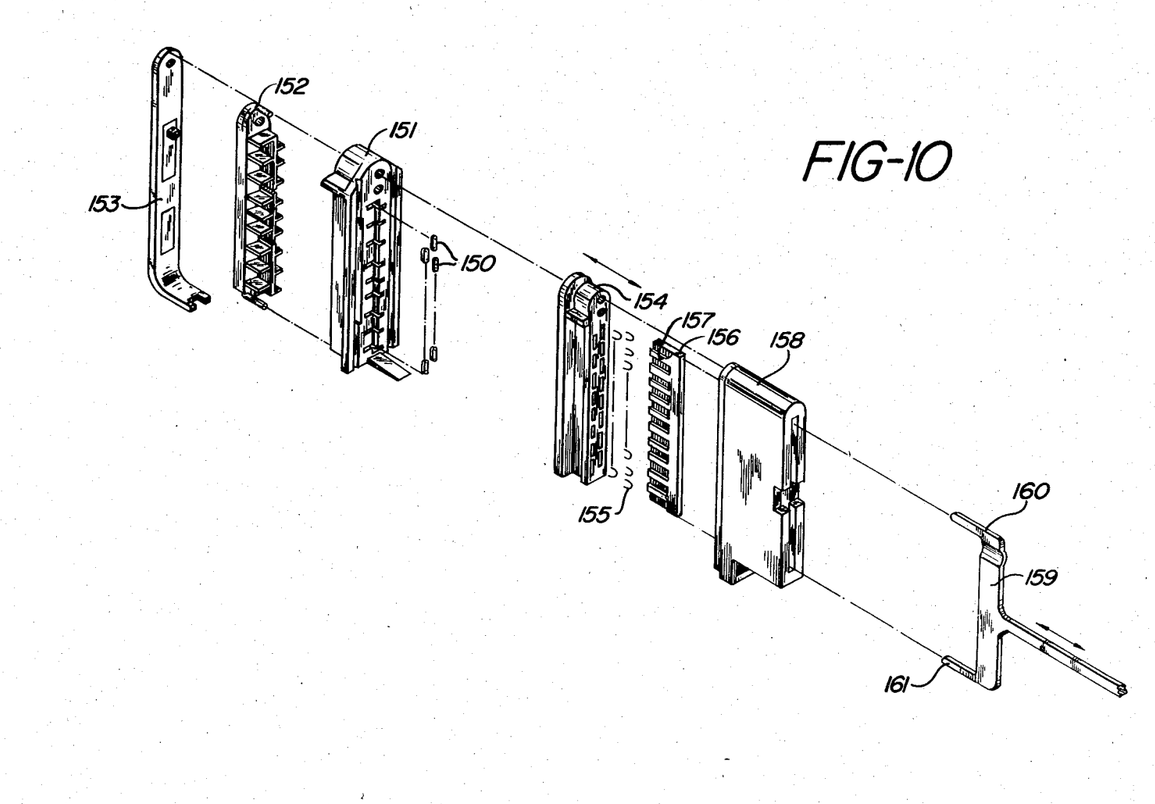
FIG. 10 is an exploded perspective view of the working parts of another embodiment of the jaws of an instrument of the present invention.

In FIG. 10 there is an exploded perspective view of another embodiment of the stationary and movable portions of the jaws for holding two-piece staples. In this embodiment the receivers 150 are held in a housing member 151 by a movable friction holding member 152 disposed within the housing. This friction member engages the outer periphery of the receivers to frictionally hold them within the housing. The receiver holding member and the friction holding member are mounted on the stationary jaw 153. A movable jaw 158 similar to that depicted in FIG. 9 comprises a staple housing member 154 for holding U-shaped staples 155. A first drive means 156 comprising individual fingers 157 which engage the staples to drive them. A second drive means 159 fits within the jaw to drive the first drive means and to also drive pins 160 and 161 at the same time that it drives the staple to cause the receiver friction holding member to move backward and disengage from the receivers allowing the receivers to be interlocked with the U-shaped staples.

An important part of the instruments of the present invention are the means disposed within the movable jaw for releasably holding individual staples in a manner to allow them to be appropriately driven through tissue to be joined and to have the legs of the staple align themselves in the openings of the receiver to interlock therewith.

Figures 11, 12:
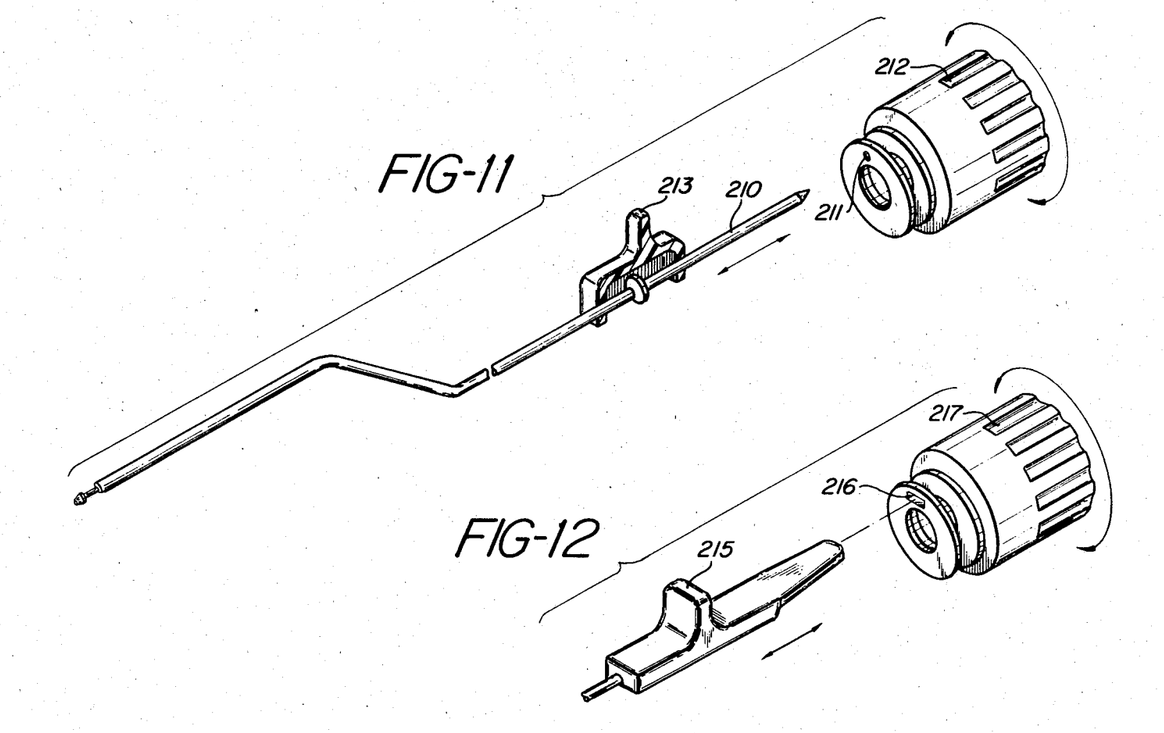
FIGS. 11 and 12 are exploded perspective views of various mechanisms for interlocking the tissue locking portion of the instrument of the present invention with the gap setting knob.

As previously discussed it is important that the tissue be clamped between the jaws and the jaws be aligned before the gap between the jaws is set. In FIGS. 11 and 12 there are shown two different embodiments for accomplishing the clamping of the tissue. In each instance, the control knob for setting the gap interlocks with a movable member. In FIG. 11 the tissue interlocking member 210 fits into an opening 211 in the knob 212. Mounted on that member is a thumb pushing member 213 having a lost motion feature to allow the member to be disengaged from the gap setting knob once it has been pushed forwardly to lock tissue in place. In FIG. 12 the thumb pushing member 215 itself fits into a slot 216 in the gap setting knob 217.

Figure 17:
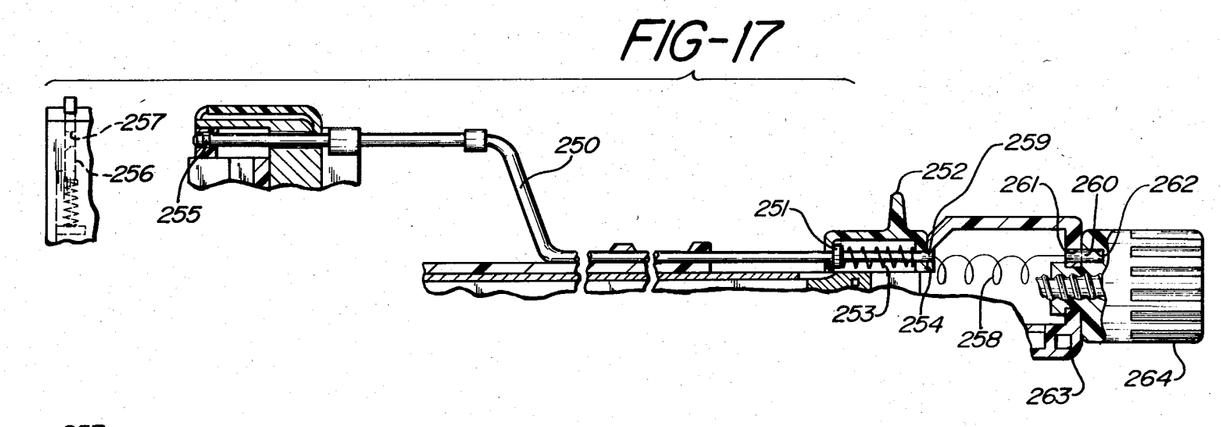
FIG. 17 is a cross-sectional view fo one embodiment of a mechanism for insuring the jaws of the instrument are properly aligned prior to the gap being set.
Figure 18:
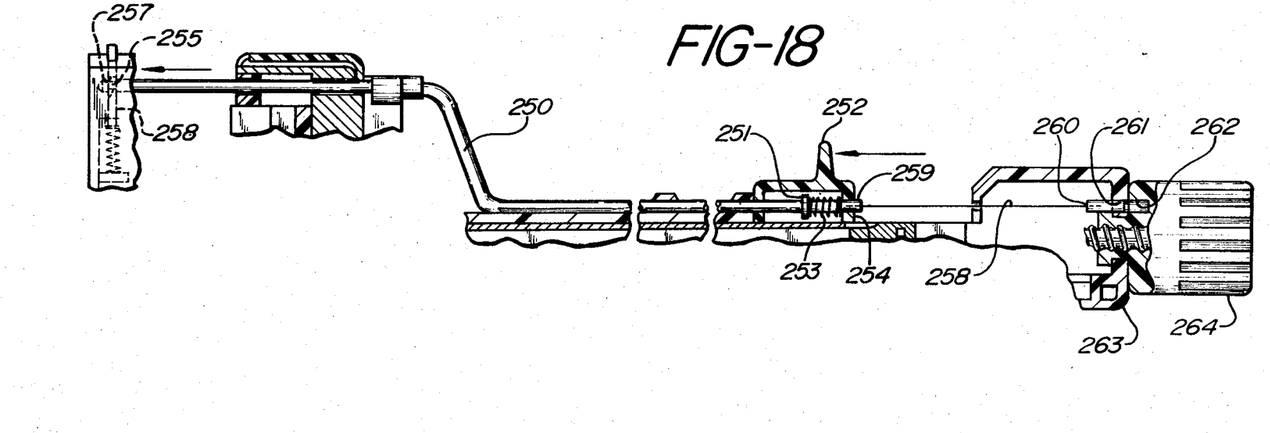
FIG. 18 is a cross-sectional view of the mechanism of FIG. 17 in the closed position.

Referring to FIGS. 17 and 18 there is shown one embodiment of a mechanism for insuring the tissue clamping means adjoins the jaws of the instrument prior to being able to set the gap. The tissue interlocking member 250 is slideably mounted on the top of the body of the instrument (not shown for the sake of clarity). Also mounted on the body of the instrument to surround the slideable member is a retaining ring 251. The ring surrounds the slideable member just inside the thumb pushing member 252 which is mounted on the slideable member. A compression spring 253 is disposed about the slideable member from the retaining ring to the back 254 of the thumb pushing member. At the front end of the slideable member is a depression 255. Mounted on the stationary jaw 256 is a suitable catch latch 257. When the slideable member is moved forwardly, the compression spring is compressed and unless the depression is grasped by the catch latch, the slideable member will return to its original position by virtue of the force of the compression spring. A cable 258 is attached at one end to the rear 259 of the slideable member and at the other end to a plug 260. The plug fits into a pair of aligned openings 261 and 262 in the instrument housing 263 and the gap setting knob 264 respectively. When the slideable member is pushed to its extreme forward position, the plug is removed from the aligned openings allowing the knob to be turned and the gap to be set.

Figure 13:
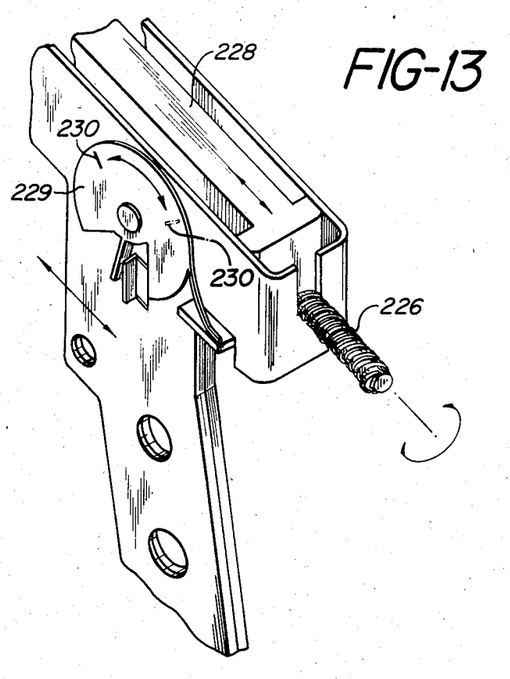
FIG. 13 is a perspective view of the inside of a portion of an instrument of the present invention depicting a gauge means for identifying the gap setting.
Figure 14:
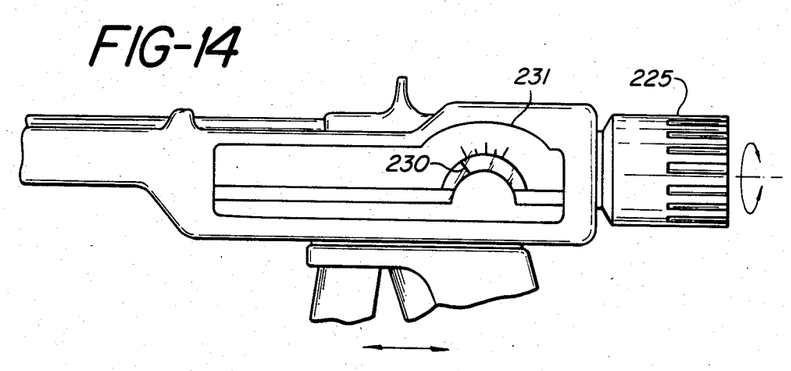
FIG. 14 is a side view of a portion of an instrument of the present invention showing the gauge for measuring the gap that has been set.

Once the tissue has been clamped between the jaws and the jaws have been interlocked and aligned and made rigid, then the gap may be set between the jaws. It is important the operating surgeon know when he has attained the appropriate gap between the jaws. In many procedures, the surgeon will be unable to see the gap during the procedure as the business end of the instrument may be deep within the surgical cavity and unobservable to the operating surgeon. Hence, in preferred embodiments of the instruments of the present invention, there is a gauge adjacent the gap setting knob. One type of gauge that is preferred with the instruments of the present invention is depicted in FIGS. 13 and 14. As the control knob 225 is turned, the screw 226 moves forward. As the desired gap of 1.2 to 1.6 milimeters is reached the pusher 228 engages a rotatable member 229. The rotatable member has a mark 230 on it. Mounted on the outside of the housing is an appropriate gauge 231. As the gap comes to the correct setting the mark on the rotatable member becomes visible within the gauge on the outside of the instrument and the surgeon can see what gap is being set.

In certain embodiments of the present invention where extremely long lines of staples are being placed such as 90 milimeter lines, the forces required to drive the full line of staples may be so great as to arch or bend the respective jaws and misalign the staples.

Figure 15:
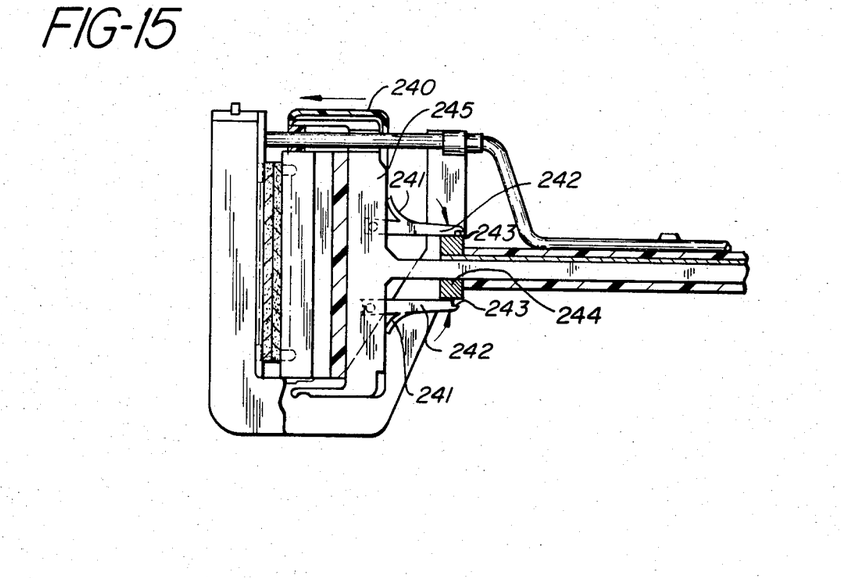
FIG. 15 is a cross-sectional view of the jaws of an instrument of the present invention with the jaws in a partially open position and including means for supporting the staple driver.
Figure 16:
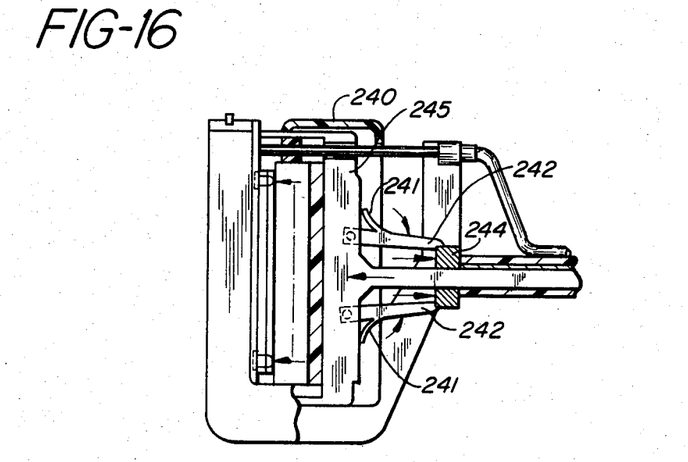
FIG. 16 is a cross-sectional view of the jaws of the instrument depicted in FIG. 15 with the jaws in a closed position.

In FIGS. 15 and 16 there is depicted a means for supporting the movable jaw once it is in position for the staples to be driven. As may be seen, mounted from the movable jaw 240 are a pair of spring mounted 241 interlocking pawl levers 242. As the movable jaw is moved into position once it reaches the appropriate gap the spring mounted pawls are driven towards each other and a step 243 or ledge at the end of the pawls interlocks with the stationary housing 244 to support the driver 245 during the actuating use of the instrument.

As may be appreciated the instruments of the present invention may be made from metals, plastics, woods, similar materials or various combinations thereof. If it is desired to make the instruments disposable, then the more inexpensive materials should be used. In most instances, it is desirable to make the instruments disposable because they are relatively complicated intricate mechanisms which are difficult to resterilize.

The general operation of the instruments of the present invention is as follows. The tissues to be joined are placed between the stationary jaw and the movable jaw and are clamped in the space therebetween by moving the tissue locking member in the direction of the stationary jaw to interlock therewith. The tissue locking member aligns the jaws and once engaged allows the gap setting knob to be turned. On turning the gap setting knob the staple housing with the staples and the pusher and drive means is moved towards the stationary jaw. An appropriate gap, generally corresponding to the thickness of the tissues to be joined, is formed between the pair of jaws and is shown on the gauge. Thereafter, the interlock on the trigger mechanism is moved out of the way and the movable handle of the trigger mechanism actuated. This action forces the head of the pusher through the staple housing forcing the staples out of their holder through the tissue so that the legs pierce the tissue and engage the openings of the receivers held by the stationary jaw. Once the staple legs are engaged in the openings of the receivers, the friction holding means of the receivers is disengaged as well as the tissue locking member. After the joining operation has been completed, the gap between the jaws is opened by turning the gap control knob in the opposite direction.

It will be obvious to those skilled in the art that various modifications and changes may be made in the invention without departing from the spirit and scope thereof. The invention is not meant to be limited by that which is shown in the drawings and described in the specification. These changes and modifications are considered to fall within the scope of the present invention as defined by the appended claims.

What is claimed is:

1. A surgical instrument for stitching tissue by means of staples, said instrument comprising: a support body, a pair of jaws mounted at one end of said support body, a staple housing mounted in one of said jaws, means mounted on said support body for moving said jaw containing said staple housing towards the other jaw to close the gap and clamp tissue placed therebetween, drive means mounted on said support body for driving the staples from the jaw on which the staple housing is mounted towards the opposite jaw, actuating means mounted at the end of said support body opposite said end on which the jaws are mounted for actuating said staple drive means, and means cooperating with the open end of said jaws to hold tissue placed therebetween while said staples are being driven, said means providing rigidity between said jaws.

2. A surgical instrument according to claim 1 including means for preventing movement of the jaw containing the staple housing to close the gap between the jaws unless the jaws are properly aligned.

3. A surgical instrument in accordance with claim 1 including means for preventing actuation of the staple drive means unless the jaws are properly aligned.

4. An instrument according to claim 1 wherein the means cooperating with the open end of said jaws to hold tissue is automatically released when the drive means has been actuated.

5. A surgical instrument according to claim 1 wherein the interlock is automatically released after the drive means has been actuated.

6. A surgical instrument according to claim 4 including means for preventing movement of the jaw containing the staple housing to close the gap between the jaws unless the jaws are properly aligned.

* * * * *